(12) United States Patent
Holt

(10) Patent No.: US 9,908,976 B2
(45) Date of Patent: Mar. 6, 2018

(54) STABLE POLYETHYLENE GLYCOL PARTICLE DISPERSIONS AND METHODS FOR FORMING THE STABLE DISPERSIONS

(71) Applicant: PSMG, LLC, Woodstock, GA (US)

(72) Inventor: Jason Holt, Ball Ground, GA (US)

(73) Assignee: PSMG, LLC, Ball Ground, GA (US)

( * ) Notice: Subject to any disclaimer, the term of this patent is extended or adjusted under 35 U.S.C. 154(b) by 29 days.

(21) Appl. No.: 14/661,104

(22) Filed: Mar. 18, 2015

(65) Prior Publication Data

US 2016/0272769 A1 Sep. 22, 2016

(51) Int. Cl.
| | |
|---|---|
| *C08J 3/11* | (2006.01) |
| *A61K 47/10* | (2017.01) |
| *A61K 9/10* | (2006.01) |
| *C08J 3/09* | (2006.01) |
| *C08L 71/02* | (2006.01) |

(52) U.S. Cl.
CPC . *C08J 3/11* (2013.01); *A61K 9/10* (2013.01); *A61K 47/10* (2013.01); *C08J 3/095* (2013.01); *C08L 71/02* (2013.01); *C08J 2371/02* (2013.01); *C08J 2471/02* (2013.01)

(58) Field of Classification Search
CPC .. A61K 9/10; A61K 47/10; C08J 3/095; C08J 3/11; C08L 71/02
USPC ................................. 524/366, 376, 377, 378
See application file for complete search history.

(56) References Cited

U.S. PATENT DOCUMENTS

| | | |
|---|---|---|
| 3,139,383 A | 6/1964 | Neville, Jr. |
| 3,843,589 A | 10/1974 | Wartman |
| 6,461,546 B1 | 10/2002 | Noid et al. |
| 8,409,586 B2 | 4/2013 | Kim et al. |
| 2002/0086919 A1 | 7/2002 | Colegrove |
| 2005/0209124 A1 | 9/2005 | Henning et al. |
| 2009/0221573 A1 | 9/2009 | Krahn et al. |
| 2014/0158633 A1 | 6/2014 | Holt |
| 2015/0027703 A1 | 1/2015 | Zhu et al. |

FOREIGN PATENT DOCUMENTS

| | | |
|---|---|---|
| WO | 9107950 A1 | 6/1991 |
| WO | 2011160996 A1 | 12/2011 |
| WO | 2015026481 A2 | 2/2015 |
| WO | 2015069773 A1 | 5/2015 |

OTHER PUBLICATIONS

Brookfield Engineering Labs, Inc., "More Solutions to Sticky Problems," © 2014.
Shangguan et al., "Morphology and Thermal Vehaviour of Poly(methyl Methycrylate)/ Poly(ethylene Glycol) Semi-interpenetration Polymer Networks," J. Chilean Chem. Soc., 56(4): 918-921, (2011).
International Search Report and Written Opinion from corresponding PCT Application No. PCT/US2016/021007, dated May 17, 2016, 16 pages.

*Primary Examiner* — Edward Cain
(74) *Attorney, Agent, or Firm* — Christensen, Fonder, Dardi & Herbert PLLC; Peter S. Dardi; Kayla Pascoe

(57) ABSTRACT

Stable dispersions of solid polyethylene glycol particles are described in polyalkylene glycol liquids. The stable dispersions have an increased viscosity relative to the liquids without the suspended particles. The stable dispersions can be formed from a melt of the polyethylene glycol particles mixed within the liquid.

26 Claims, 2 Drawing Sheets

STABLE POLYETHYLENE GLYCOL PARTICLE DISPERSIONS AND METHODS FOR FORMING THE STABLE DISPERSIONS

FIELD OF THE INVENTION

The invention relates to stable dispersions of polyethylene glycol (PEG) particles in a solvent in which the particles are insoluble, such as liquid polyalkylene glycols. The invention further relates to methods for forming the stable dispersions.

BACKGROUND OF THE INVENTION

Polyethylene glycol, copolymers thereof and other polyalkylene glycols as well as compositions incorporating these polymers find wide use due to desirable properties for various uses along with their low toxicity. Low molecular weight polyethylene glycols are liquids at room temperatures, but higher molecular weight polyethylene glycols are room temperature solids with a relatively low melting point. Very high molecular weight polyethylene glycols, also referred to as polyethylene oxides, can exhibit flocculating properties. Both liquid and solid forms of polyethylene glycols find use in the pharmaceutical applications.

SUMMARY OF THE INVENTION

In a first aspect, the invention pertains to a dispersion comprising at room temperature a solvent and stably suspended polyethylene glycol particles wherein the solvent comprises liquid polyalkylene glycol, and having a particle concentration of at least about 0.01 weight percent. Also, the invention can pertain to a method for forming a suspension of organic particles, e.g., polymer particles or pharmaceutical particles, soluble insoluble in polyalkylene glycol, and optionally soluble in water, in which the method can comprise blending organic particles into the stable dispersion of claim 1 to form a suspension of the organic particles in the stable dispersion.

In a further aspect, the invention pertains to a method for forming a stable dispersion of polyethylene glycol particles in a room temperature liquid comprising a polyalkylene glycol, the method comprising forming a melt blend of a room temperature solid polyethylene glycol at a temperature above the melting point of the polyethylene glycol in a solvent comprising liquid polyalkylene glycol and cooling the melt to resolidify solid polyethylene glycol particles having a complex morphology.

In another aspect, the invention pertains to a dispersion comprising at room temperature stably dispersed particles of polyethylene glycol having a visibly complex and high surface area morphology and liquid polyethylene glycol.

DETAILED DESCRIPTION

Figure 1:
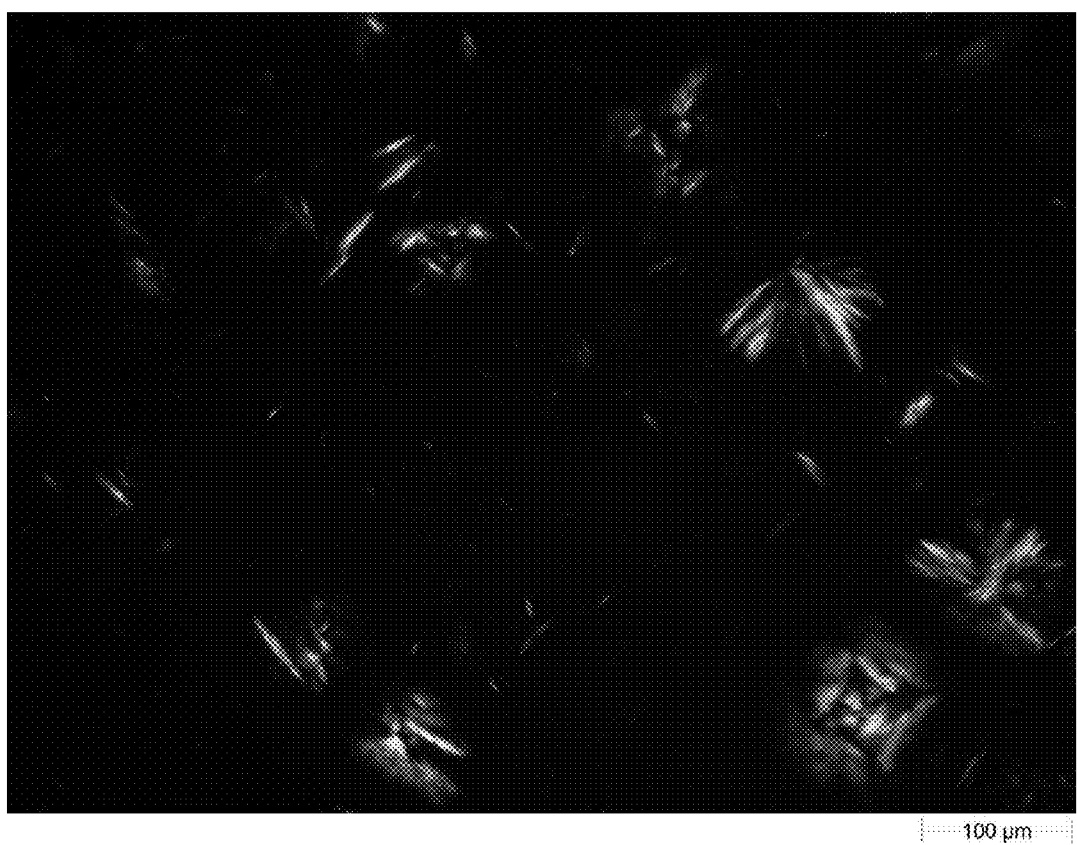
FIG. 1 is a photograph of an image through an optical microscope of a stable dispersion taken with polarized light with structured polyethylene glycol particles visible throughout the dispersion in bright illumination suggesting crystalline structure of the particles.

Dispersions have been formed of polyethylene glycol (PEG) particles stably dispersed in a liquid polyalkylene glycol dispersant, which can be effective to increase the viscosity of the liquid for appropriate applications. It has been discovered that polyethylene glycol particles with complex structures suggesting a very high surface area can be formed directly by solidifying a melt of the polymer within a liquid polyalkylene glycol. The higher molecular weight polyethylene glycol compositions are insoluble in the liquid polyalkylene glycols, and the solidifying particles naturally form with complex structures suggestive of snow flakes that remain suspended in the liquid in a stable dispersion. Higher molecular weight polyethylene glycols are solids at room temperature, but with a melting point at modest temperatures, generally below 70° C. for relevant polymers, which is correspondingly well below the boiling point of relevant liquid polyalkylene glycols. The solidification process of the particles within the liquid naturally results in complex structured polyethylene glycol particles, and while not wanting to be limited by theory, the complex, presumably high surface area, particles may contribute to the stability of the dispersion. The resulting dispersion can be useful as a more viscous substitute for polyalkylene glycol liquids with equivalent solubility properties.

Polyethylene glycol (PEG), polyethylene oxide (PEO), or poly(oxyethylene) (POE) refers to an oligomer or polymer of ethylene oxide. The three names are chemically synonymous, but historically PEG has tended to refer to oligomers and polymers with a molecular mass below 20,000 g/mol, PEO to polymers with a molecular mass above 20,000 g/mol, and POE to a polymer of any molecular mass. Polyethylene oxide (or PEG or POE) can be represented by the formula H—(O—CH$_2$—CH$_2$)$_n$—OH, where n refers to the degree of polymerization, and for high molecular weight polymers, n is large, while for liquid PEG n is roughly no more than about 15-20. Particular polymer samples generally have a distribution of molecular weights. The nature of a polymer sample can be characterized by the average molecular weight and suitable polymers can be linear or branched. Copolymers can be formed with other alkylene oxides.

PEG compositions can be liquids or low melting solids, depending on the molecular weights of the polymer. For example, PEG 400 generally refers to a PEG formulation with an average molecular weight between 380 g/mole and 420 g/mole. PEG 400 is commercially available, for example, as Dow CARBOWAX™ PEG 400 or BASF PLURIOL® E 400. PEG 600 generally refers to a PEG formulation with an average molecular weight between 570 g/mole and 630 g/mole. Above a molecular weight of roughly 800 g/mole, PEG can be a waxy paste like material at room temperature. PEG with molecular weights above about 800 g/mole are waxy room temperature solids. Lower molecular weight PEO, such as from 20,000 g/mol to 50,000 g/mol can be suitable as solids in the viscous dispersions described herein. The melting points of the relevant room temperature solid polymers are only weakly dependent on molecular weight, and polymers of interest generally melt at temperatures of no more than about 70° C. and more specifically to PEGs have a melting point that seems to plateau at about 67° C. Polypropylene glycols with molecular weights no more than about 20,000 g/mole are generally room temperature liquids. But some polyethylene glycol—polypropylene glycol or other similar copolymers may be suitable as solid polymers for use in the dispersions described herein. For use as room temperature solid polymer particles in the dispersions described herein, unless explicitly indicated otherwise, PEG is used to refer to room temperature solid polymers with a majority of polyethyelene oxide repeat units in the polymer a molecular weight of no more than about 50,000 g/mol and a melting point of no more than about 85° C.

Polyethylene glycol polymers have the interesting property that higher molecular weight solid forms of the polymer do not dissolve in the lower molecular weight polymer liquids. Thus, particles of the higher molecular weight polymers can be suspended as particles in the PEG liquids and other polyalkylene glycol liquids. In general, polyethylene glycol particles as commercially available settle out of a dispersion in a polyalkylene glycol dispersion without mixing, although the particles can possibly be stabilized in the dispersion with the addition of significant quantities of viscosity modifying agents that may not be desirable for many applications. The polyethylene glycol class of polymers are desirable for many applications due to their environmentally benign nature and very low toxicity. These polymers are used in the formulation of pharmaceuticals and PEO powders are used as laxatives including in over the counter products. It has been discovered how to form stable dispersions of polyethylene glycol particles in a polyalkylene glycol liquid.

Polyalkylene glycol liquids, especially polyethylene glycol liquids, can be desirable carrier fluids do to their low toxicity and commercial availability. These liquids though have a limited range of viscosity, which for polyethylene glycol liquids can be due to a corresponding limited range of molecular weights that are liquids. It has been discovered that a stable dispersion of polyakylene glycol liquids with PEG particulates can be an effective way of increasing the viscosity of the polyalkylene glycol liquids. As described herein, the polyethylene glycol particle dispersions are stable so that the dispersions can be effectively used as a liquid dispersant for corresponding applications with a desired higher viscosity. Thus, since the inherent viscosity of the polyethylene glycol liquids cannot be directly changed, the liquid can be augmented with stable suspended particulates to increase the viscosity of suspension, which can be effectively a colloid.

The polyethylene glycol particles that form by solidification from a melt in solution have been found to have elaborate structures with tendrils and/or highly open structures which visibly indicate high surface areas. Microscope images of representative particles are shown below. The high surface area can be rationalized as contributing to the stability of the dispersion. Viewing the particles with polarized light suggests that the solidified polyethylene glycol particles are crystalline. The particle sizes vary over a significant range and also have a variety of shapes with some of the particles having a thin dimension as a flake. The stable dispersion of the polyethylene glycol particles exhibits colloid behavior even though the particles are larger than traditional colloid particles, and the stability may be a function of the viscosity of the fluid component as well as the large surface area of the particles and density of the crystalline material forming the particles.

In contrast to the stable dispersions described herein, stable suspensions of PEO have been described in U.S. Pat. No. 3,843,589 to Wartman (Wartman '589 patent), entitled "Stable Pumpable Slurries of Ethylene Oxide Polymers," incorporated herein by reference. To achieve the stable suspension, the Wartman '589 patent described a more complex liquid with property modifying additives to achieve a suitable density. In contrast, the present stable dispersions can be formed with unmodified polyethylene glycol or the like to form the stable dispersions.

For commercial polyethylene oxide particulates, PEO fines have an average particle size on the order of 25 microns. Polyethylene oxide fines are considered hazardous for handling due to the possibility of the particles becoming airborne. The present submicron PEG/PEO particles are generated directly in a liquid so the handling problems can be avoided. It is believed that the high surface area particles of polyethylene glycol formed in the present processes are unique. While the particles can be removed from the stable suspensions, the dried particles have not been separately characterized at this time.

Since the viscosity of the liquid is effectively increased through the stable suspension of the polyethylene glycol particles, the effective liquid can be useful to form suspensions of insoluble organic particles. Effective liquid refers to the stable dispersions that are useful as higher viscosity version of the liquids. Due to the effective higher viscosity, the suspensions of organic particles, even if not stable in the suspension generally settle more slowly as a result of the higher viscosity. This relative stabilization can be desirable from a processing perspective. In some embodiments, the organic particles are soluble in water so that the suspension can be totally soluble in water, which can relate to the application of the suspension. In some embodiments, the organic particles can be polymers soluble in water but insoluble in at least the relevant polyalkylene glycol, or other organic compounds such as pharmaceuticals.

A representative use of liquid polyethylene glycol for a pharmaceutical preparation is described in U.S. Pat. No. 8,409,586 to Kim et al., entitled "Stable Liquid Formulation of Human Growth Hormone," incorporated by reference. Polyalkylene glycol liquid have found desirable uses for the delivery of flocculating agents as described in published U.S. patent application 2014/0158633A1 to Holt, entitled "Particle Suspensions of Flocculating Polymer Powders and Powder Flocculant Polymer Blends," incorporated herein by reference. The stable particle dispersions described herein can be used as substitutes for liquid polyalkylene glycol liquid in various applications.

Stable Dispersions and their Properties

The stable dispersions of polyethylene glycol particles comprise a polyalkylene glycol liquid. The suspensions of the solid PEG particles in the polyalkylene glycol liquid can have a solid concentration from about 0.01 weight percent to about 20 weight percent, in further embodiments from about 0.025 weight percent to about 17 weight percent and in additional embodiments from about 0.1 weight percent to about 15 weight percent. A person of ordinary skill in the art will recognize that additional ranges of solids concentrations within the explicit ranges above are contemplated and are within the present disclosure. As noted in the Examples below, Applicant has obtained stable dispersions with about 10 wt % solid PEG particles and extrapolation of this work indicates utility for the ranges above. However, at very high solid contents, the solids can effectively dissolve the liquids to form a waxy solid. Specifically, Dow CARBOWAX™ 540 Blend is a blend of 60 wt % PEG 1450 (solid) and 40 wt % PEG 300 (liquid), which is a soft solid.

As the molecular weights of polyethylene glycol increase, the melting temperature tends to level off. Thus, the melting point of higher molecular weight polyethylene glycols plateau at roughly 65° C. As used herein, the traditional divisions between polyethylene glycol and polyethylene oxide are not of great relevance, so the solid polyethylene glycol particles for the stable dispersions can have average molecular weight up to about 50,000 g/mole. In some embodiments, the average molecular weights of the solids can be no more than about 40,000 g/mole, in further embodiments from about 800 g/mole to about 30,000 g/mole, and in other embodiments from about 1500 g/mole to about 25,000 g/mole. Copolymers of polyethylene glycol are known, such as copolymers with polypropylene glycol, although the polypropylene glycols remain liquid until significantly higher molecular weights. However, room temperature solid polyethylene glycol copolymers with at least about 80% ethylene glycol based repeat units (—O—$CH_2$—$CH_2)_n$—) in the polymer are considered ethylene glycol polymers as used herein, although in embodiments of particular interest, the solid particles are homopolymers of polyethylene glycol due to a low toxicity. In some embodiments, the polymers have at least about 85% ethylene glycol based repeat units, in further embodiments at least about 90% ethylene glycol repeat units, and in other embodiments at least about 95% ethylene glycol based repeat units. A person of ordinary sill in the art will recognize that additional ranges of average molecular weights and polymer composition within the explicit ranges above are contemplated and are within the present disclosure.

The liquid of the stable dispersons generally comprises a liquid polyalkylene glycol, i.e., polyether polyol, e.g., diol or triol, with oxyethylene repeat units along the polymer backbone, which generally have moderate molecular weights, such as polyethylene glycol (PEG, HO—($CH_2$—$CH_2$—O—$)_n$H), propylene glycol (PPG, HO—($CH_2$—$CHCH_3$—O—$)_n$H), copolymers thereof or a mixture thereof (PEG/PPG) as the primary component or only component. PEG and PPG are ethers with two terminal hydroxyl groups and can be moderately viscous compositions, which influences the viscosity of the suspension. Glyceryl ether polymers are commercial polymers with PEG or PPG reacted with a glycerine molecule to form an ether linkage with the resulting molecule having three terminal hydroxyl groups. (Dow®, PT-series of polymers). Specifically, the liquid of the suspension can comprise at least about 75 weight percent, in further embodiments at least about 80 weight percent and in additional embodiments at least about 90 weight percent PEG/PPG. Polymers generally have a distribution of molecular weights, and liquid PEG generally has an average molecular weight from about 200 g/mole to about 700 g/mole and in further embodiments from about 300 g/mole to about 650 g/mole. PEG 400 (average molecular weight 380-420), PEG 600 (average molecular weight 580-620) and mixtures thereof can be effectively used. Polypropylene glycols can have suitable viscosities at average molecular weights in the several thousands, and are commercially available, for example, from Dow Chemical and BASF PLURIOL P® series. Glyceryl ether polymers with three terminal hydroxyl groups are similarly commercially available with similar viscosities and other properties. Also, copolymers ethylene oxide and propylene oxide are commercially available. The liquid can be selected to not significantly dissolve the solid polymer particles.

Liquids of particular interest can be liquid polyalkylene glycols or mixtures thereof, in which liquid polyethylene glycols are of interest due to low toxicity. Of course, liquids generally contain some contaminants, such as unreacted monomers and other compounds, in small amounts, and these are not considered in the art distinct from the specified liquids. However, in some embodiments, additional liquids can be blended with the polyalkylene glycols. Generally, the liquid comprise at least 75 weight percent polyalkylene glycols, in further embodiments at least about 85% polyalkylene glycols and in other embodiments at least about 95 weight percent polyalkylene glycols. Suitable additional liquids include, for example, propylene glycol, ethylene glycol, glycerol and the like, which dissolve into the polyalkylene glycol and do not dissolve the solid polyethylene glycol. A person of ordinary skill in the art will recognize that additional ranges of liquid concentrations within the explicit ranges above are contemplated and are within the present disclosure.

The commercial polyalkylene glycols generally have reported viscosity values at elevated temperatures, such as at 99° C., although for many applications the room temperature viscosity is of significant interest. For the stable dispersion described herein, the dispersed polyethylene glycol particles generally melt below 99° C., so viscosities at room temperature are appropriate values also from the perspective of making meaningful viscosity measurement for the dispersion rather than a melt of the dispersion. Therefore, unless indicated otherwise, viscosity measurements are provided at room temperature.

The viscosity of the dispersion can depend on the concentration of the dispersed solids and possibly on the processing conditions as well as the liquid composition. As noted in the Example below, both a polyethylene glycol liquid and a corresponding stable dispersion are observed to have room temperature shear thickening, non-Newtonian, behavior, although it is not clear if all relevant samples exhibit this non-Newtonian behavior. Thus, for the non-Newtonian samples, the viscosity increases at higher shear used in the measurement of the shear viscosity. Polypropylene glycols remain liquid at higher molecular weights and some of these liquids have reported room temperature viscosities with relatively high values at low shear. Viscosities as reported herein are Brookfield viscosities measured with rotating spindles. Due to the non-Newtonian behavior observed for the room temperature liquids and dispersions, these viscosities measured with rotation based viscometers have measurements that depend on the specific spindle. See, "More Solutions to Sticky Problems," Brookfield Engineering Labs, Inc., Copyright 2014, incorporated herein by reference. Reported Brookfield viscosities with rpm and spindle specified are reproducible and well defined and re relied upon accordingly. The viscosity at room temperature (about 22° C.) of the stable dispersion can be with a shear of 6 rpm at least about 20 cP, in further embodiments at least about 25 cP, in additional embodiments at least about 30 cP and in other embodiments from about 35 cP to about 1500 cP, and with a shear of 20 rpm at least about 200 cP, in further embodiments at least about 250 cP and in additional embodiments from about 300 cP to about 3000 cP. Viscosity measurements at 6 rpm can be obtains with a #1 LVT spindle, and viscosity measurements at 20 rpm can be obtained with a #2 rvt spindle. Alternatively, the viscosity can be viewed from the perspective of the increase in viscosity obtained with the dispersion relative to the liquid without the dispersed PEG solids. The results in the Example below suggest that the room temperature shear thickening behavior is somewhat less pronounced for the stable dispersions than for polyethylene glycol itself. In some embodiments, the room temperature viscosity with a shear of 20 rpm increases at least a factor of 1.5, in further embodiments at least a factor of 2 and in additional embodiments at least a factor of 2.5 relative to the liquid without the stably dispersed PEO particles. A person of ordinary skill in the art will recognize that additional ranges of viscosity and factors of viscosity increase are contemplated and are within the present disclosure.

Processing to Form Stable Dispersions and Dispersion Properties

The basis for forming the suspensions involves the solidification of the room temperature solid polymer particles in situ within a liquid. The melt blend can be formed in various ways as described in the following. The melt blend then is allowed to cool. The resulting particles naturally form with a small particle size based on the processing itself. Once the blend cools a natural colloid can be formed with a cloudy appearance. The stable dispersion can be used as a more viscous liquid for corresponding applications where a more viscous liquid is desirable.

The initial melt can be formed in any of several ways. The objective is to have a reasonably mixed melt of the (room temperature) solid polyethylene glycol blended with the dispersion liquid at a temperature above the melting point of the solid PEG. The melted polyethylene glycol generally can be soluble in the dispersion liquid so that the melted state a clear uniform liquid can be formed. Several processing approaches can be used to form the well mixed melt. Specifically, the polyethylene glycol solids can be added to the liquid prior to or after heating the liquid. Similarly, the room temperature solid polymer may or may not be melted prior to the addition to the liquid. In general, the melt blend can be heated to a temperature of at least about 60°, in some embodiments at least about 65° C. and in other embodiments from about 70° C. to about 95° C. As an alternative expression, the temperature of the melt blend can be at least one degree above the melting point of the room temperature solid PEG, in further embodiments at least about 2 degrees above the melting point of the solid PEG and in additional embodiments, from about 3 degrees to about 25 degrees above the melting point of the room temperature solid PEG. A person of ordinary sill in the art will recognize that additional temperature ranges within the explicit ranges above are contemplated and are within the present disclosure. Of course, higher temperatures below the flash point or boiling point of the liquid can be used but higher temperatures involve the use of additional energy which would be wasted upon cooling.

As a further approach to reduce energy consumption, only an appropriate fraction of the liquid may be heated. As long as the concentration of room temperature solid is at an acceptable level for forming particles that form a stable dispersion, additional liquid can be added after cooling to provide the desired concentration of resolidified particles and corresponding fluid properties, such as viscosity. Since only a fraction of the desired final liquid is heated, less energy is expended to form the melt, which becomes lost heat upon cooling.

In some embodiments, the melt blend can be mixed for a suitable period of time to obtain a well blended mixture. In the Example below, the melt blend is mixed for an hour, although in some embodiments, the melt blend is mixed for at least about 2 minutes, in further embodiments for at least about 5 minutes and in additional embodiments from about 8 minutes to about 4 hours. Various suitable mixing devices can be appropriately used, such as commercially available mechanical mixers. In additional or alternative embodiment, the room temperature solid polyethylene glycol can be added as a powder or melt into a flow of the liquid polyalkylene glycol, such as heated polyalkylene glycol, such as in a pipe or the like, in which turbulence of the flow performs suitable blending, which may or may not be supplemented with additional mixing. In general, reasonable blending can be achieved through any suitable approach. The melt blend can appear to be a clear liquid. The appearance suggests that the melted solid polymer is dissolved in the liquid, although the liquids are expected to have virtually identical indices of refraction, which may complicate visual observations.

Once the melt blend is well mixed, the liquid can be cooled or allowed to cool back to room temperature. In the Example, the liquid is stirred continuously while the particle precipitate from the solution, but stirring may or may not be performed during the cooling. Also, specific refrigeration may or may not be used, but good airflow can facilitate cooling. As the liquid cools, the appearance can change to look cloudy as the solid polymer particles form from the melt. Generally, the resulting dispersion is stable with no visible settling of particles after at least about 1 hour, in further embodiments after at least about one day and in other embodiments after at least about a week or longer. As noted in the Example below, a stable dispersion has been observed to exhibit no visible settling after more than a month. A person of ordinary skill in the art will recognize that additional ranges of dispersion stability within the explicit ranges above are contemplated and are within the present disclosure. Based on the stability of the resulting dispersion, the dispersion can be used as a more viscous version of the liquid. Then, the dispersion can be carried forward accordingly for selected uses.

EXAMPLE

This Example demonstrates the formation of a viscous stable dispersion of room temperature solid PEG within a PEG liquid.

CARBOWAX™ PEG 300 (Dow Chemical) was heated to roughly 65° C. in a flask on a hot plate. About 2.5 weight percent CARBOWAX™ PEG 3350 powder was added to the heated PEG 300 and stirred with a mechanical stirrer for roughly an hour. The hot mixture was a clear liquid. After an hour of stirring, the mixture was allowed to cool back to room temperature without refrigeration. The cooled liquid turned cloudy, but no solids settled from the dispersion. The cloudy liquid was observed to be viscous. The cloudy dispersion has been kept for more than a month without observation of any settling. Experiments were also performed at concentrations up to about 10 wt % PEG 3350, but more extensive evaluations were performed for the 2.5 wt % samples.

The cloudy dispersion was analyzed to evaluate its properties. The viscosity was measured at room temperature using a Brookfield Viscometer for both the PEG 300 alone and the stable dispersion. PEG viscosities are generally reported in product literature at elevated temperatures, e.g., 99° C., but at elevated temperatures, the PEG 3350 melts. Also, for later processing using the PEGs at room temperature, the room temperature values are particularly meaningful. The viscosities were measured at two different values of shear, 6 rpm (#1 LVT spindle) and 20 rpm (#2 RVT spindle). The changes in viscosities indicate a shear thickening, i.e., non-Newtonian, fluid behavior for both the neat PEG 300 and the PEG 300/2.5% PEG 3350 stable dispersion. The measured room temperature viscosities were as follows: PEG 300-6.4 cP (6 rpm) and 100 cP (20 rpm) and stable dispersion (PEG 300/2.5% PEG 3350-81 cP (6 rpm) and 672 cP (20 rpm).

Figure 2:
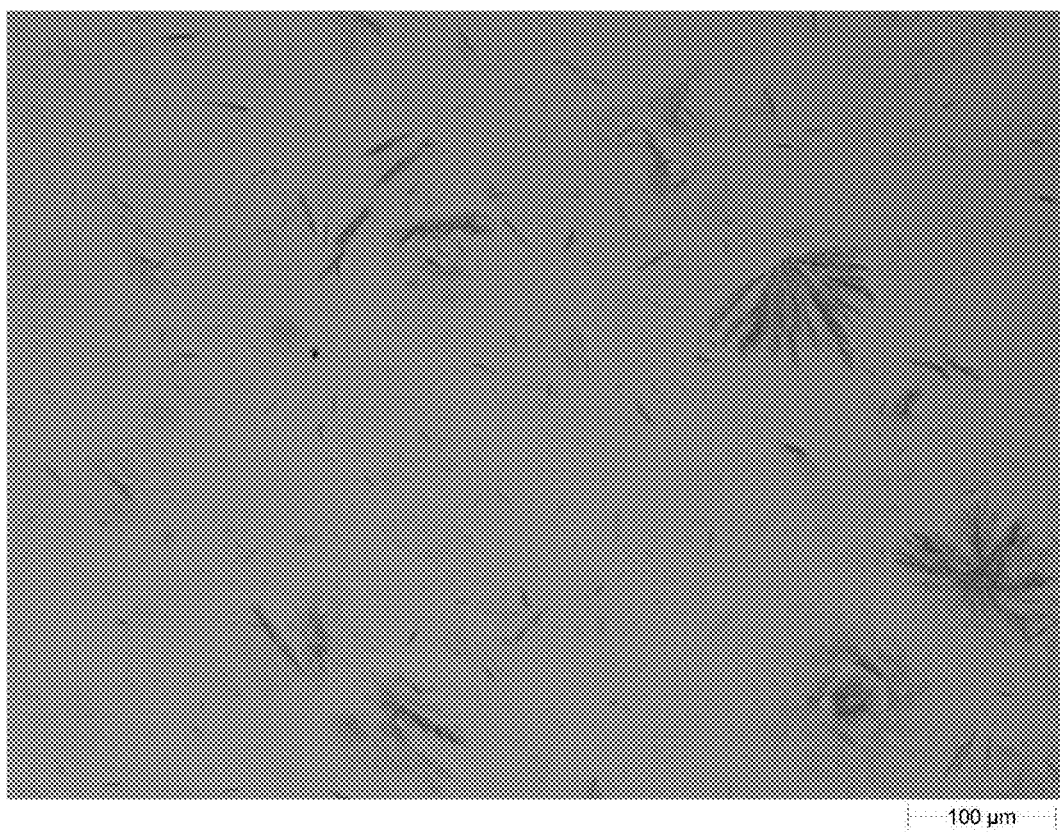
FIG. 2 is a photograph of the image of FIG. 1 taken with un-polarized light.

Optical microscope images were obtained for the stable dispersion to examine the nature of the dispersed particles of solidified PEG. FIG. 1 shows a micrograph taken with polarized light, and FIG. 2 is a corresponding image with un-polarized light. The bright images observed with the polarized light suggest that the particles comprise crystalline PEG in the particles. The particles are observed to have complex structures reminiscent of snowflakes that visibly suggest high surface areas. The high surface area may contribute to the stability of the dispersion. Complex structures of crystalline PEG have been observed in blends of PEG and polymethylmethacrylate. See Shangguan et al., J. Chilean Chemical Society, 54(4), 918-921 (2011). Since the index of refraction of the liquid and solid particles are essentially identical, optical scattering measurements to evaluate particle size distribution cannot be performed. However, based on the complex structure of the particles, it may not be possible to interpret the scattering data in a meaningful way even if the scattering data could be obtained since assumptions used to evaluate scattering data may not hold for the snow flake like particles of the solidified PEG particles.

The embodiments above are intended to be illustrative and not limiting. Additional embodiments are within the claims. In addition, although the present invention has been described with reference to particular embodiments, those skilled in the art will recognize that changes can be made in form and detail without departing from the spirit and scope of the invention. Any incorporation by reference of documents above is limited such that no subject matter is incorporated that is contrary to the explicit disclosure herein.

What is claimed is:

1. A dispersion comprising at room temperature a solvent and stably suspended polyethylene glycol particles wherein the solvent comprises liquid polyalkylene glycol, and having a particle concentration from about 0.01 weight percent to 7 weight percent, wherein the polyethylene glycol particles have an average molecular weight of 800 g/mole to about 50,000 g/mole.

2. The dispersion of claim 1 wherein the polyethylene glycol particles have an average molecular weight of 800 g/mole to about 10,000 g/mole.

3. The dispersion of claim 1 wherein the polyethyene glycol particles have a visibly complex, high surface area structure.

4. The dispersion of claim 1 wherein the liquid polyalkylene glycol comprises polyethylene glycol.

5. The dispersion of claim 1 wherein the liquid is polyethylene glycol.

6. The dispersion of claim 1 wherein the particle concentration is from about 0.2 weight percent to about 6 weight percent.

7. The dispersion of claim 1 wherein the particle concentration is from about 0.25 to about 5 weight percent.

8. The dispersion of claim 1 wherein dispersion is stable with no settling of particles without stirring for at least about 1 days.

9. The dispersion of claim 1 having a room temperature shear thickening viscosity.

10. The dispersion of claim 1 having a viscosity at a shear of 6 rpm with a Brookfield #1 LVT spindle of at least 20 cP.

11. The dispersion of claim 1 having a viscosity at a shear of 20 rpm with a Brookfield #2 rvt spindle of at least about 200 cP.

12. The dispersion of claim 1 having a viscosity at a shear of 6 rpm with a Brookfield #1 LVT spindle that is at least a factor of 2 greater than the viscosity of the corresponding room temperature liquid without the dispersed particles.

13. A method for forming a suspension of organic particles insoluble in polyalkylene glycol, the method comprising blending organic particles into the stable dispersion of claim 1 to form a suspension of the organic particles in the stable dispersion.

14. A method for forming a stable dispersion of polyethylene glycol particles in a room temperature liquid comprising a polyalkylene glycol, the method comprising:
    forming a melt blend of a room temperature solid polyethylene glycol at a temperature above the melting point of the polyethylene glycol in a solvent comprising liquid polyalkylene glycol wherein the melt blend has a room temperature solid polyethyene glycol concentration of no more than 7 weight percent; and
    cooling the melt to resolidify solid polyethylene glycol particles.

15. The method of claim 14 wherein the heating is performed to a temperature of no more than about 95° C. and wherein the cooling is performed by exposing the melt blend to the ambient to allow the melt blend to cool.

16. The method of claim 14 wherein the polyethylene glycol particles have an average molecular weight of no more than about 50,000 g/mole and wherein the resolidified solid polyethylene glycol particles have a visibly complex and high surface area morphology.

17. The method of claim 14 wherein the dispersion has a particle concentration of no more than about 6 weight percent and wherein the polyalkylene glycol liquid comprises polyethylene glycol liquid.

18. The method of claim 14 wherein the dispersion is mixed during the resolidification of the polyethylene glycol particles.

19. A method for forming a stable dispersion of polyethylene glycol particles in a room temperature liquid comprising a polyalkylene glycol, the method comprising:
    forming a melt blend of a room temperature solid polyethylene glycol at a temperature above the melting point of the polyethylene glycol in a solvent comprising liquid polyalkylene glycol wherein the room temperature solid polyethylene glycol is melted prior to the addition to the polyalkylene glycol liquid; and
    cooling the melt to resolidify solid polyethylene glycol particles.

20. The method of claim 14 wherein the room temperature solid polyethylene glycol is added as a power to the liquid polyalkylene glycol.

21. The method of claim 20 wherein the liquid polyalkylene glycol liquid is heated above the melting point of the polyethylene glycol prior to the addition of the powder to the liquid.

22. A dispersion comprising at room temperature stably dispersed particles of polyethylene glycol having a visibly complex and high surface area morphology and liquid polyethylene glycol, and having a particle concentration from about 0.01 weight percent to 7 weight percent.

23. The dispersion of claim 22 wherein the polyethylene glycol particles have an average molecular weight of 800 g/mole to about 50,000 g/mole.

24. The dispersion of claim 22 wherein the particle concentration is from about 0.2 weight percent to about 5 weight percent.

25. The dispersion of claim 22 having a room temperature shear thickening viscosity wherein the viscosity at a shear of 6 rpm with a Brookfield #1 LVT spindle of at least 20 cP.

26. The method of claim 13 wherein the organic particles comprise a flocculant polymer or a pharmaceutical.

* * * * *